US009155616B2

(12) United States Patent
Venkatasubramanian et al.

(10) Patent No.: US 9,155,616 B2
(45) Date of Patent: Oct. 13, 2015

(54) PROSTHETIC HEART VALVE WITH EXPANDABLE MICROSPHERES

(71) Applicant: St. Jude Medical, Cardiology Division, Inc., St. Paul, MN (US)

(72) Inventors: Ramji T. Venkatasubramanian, Maple Grove, MN (US); Eunhee Cho, Vadnais Heights, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 14/136,091

(22) Filed: Dec. 20, 2013

(65) Prior Publication Data

US 2014/0243969 A1    Aug. 28, 2014

Related U.S. Application Data

(60) Provisional application No. 61/770,502, filed on Feb. 28, 2013.

(51) Int. Cl.
*A61F 2/24* (2006.01)
(52) U.S. Cl.
CPC ............... *A61F 2/24* (2013.01); *A61F 2/2412* (2013.01); *A61F 2210/0061* (2013.01)
(58) Field of Classification Search
CPC ... A61F 2/2439; A61F 2/2418; A61F 2/2442; A61F 2/44
USPC ........................................................ 623/2.37
See application file for complete search history.

(56) References Cited

U.S. PATENT DOCUMENTS

| 4,692,164 | A | * | 9/1987 | Dzemeshkevich et al. ... 623/2.14 |
| 4,878,907 | A | * | 11/1989 | Okada et al. .................. 623/1.44 |
| 5,702,454 | A | * | 12/1997 | Baumgartner ................. 128/898 |
| 7,018,406 | B2 | | 3/2006 | Seguin et al. |
| 7,329,279 | B2 | | 2/2008 | Haug et al. |
| 2004/0091543 | A1 | | 5/2004 | Bell et al. |

(Continued)

FOREIGN PATENT DOCUMENTS

| WO | 2009042196 A2 | 4/2009 |
| WO | 2011057087 A1 | 5/2011 |
| WO | 2013033791 A1 | 3/2013 |

OTHER PUBLICATIONS

Extended European Search Report for Application No. 14153238..2 dated Apr. 3, 2014.

*Primary Examiner* — Thomas J Sweet
*Assistant Examiner* — Wade P Schutte
(74) *Attorney, Agent, or Firm* — Lerner, David, Littenberg, Krumholz & Mentlik, LLP

(57) ABSTRACT

A prosthetic heart valve includes a valve assembly mounted to an expandable stent. The prosthetic heart valve includes a cuff coupled to the stent. The cuff includes a pocket formed between an outer side and an inner side of the cuff. The pocket includes a plurality of biocompatible and irreversibly expandable microspheres. After implantation of the prosthetic heart valve into a patient, any gaps existing between the cuff and the native heart valve are exposed to bodily fluid, such as blood. The blood enters the pocket of the cuff through pores in the outer side of the cuff. The blood interacts with the microspheres, causing irreversible expansion of the microspheres. The microspheres expand to fill any gaps between the prosthetic heart valve and the native heart tissue, sealing the gaps and preventing leakage through the gaps.

17 Claims, 5 Drawing Sheets

(56) References Cited

U.S. PATENT DOCUMENTS

2004/0215318 A1 10/2004 Kwitkin
2010/0185277 A1 7/2010 Braido et al.
2012/0078352 A1 3/2012 Wang et al.
2013/0331929 A1* 12/2013 Mitra et al. ................. 623/2.11
2014/0222144 A1* 8/2014 Eberhardt et al. ........... 623/2.38

* cited by examiner

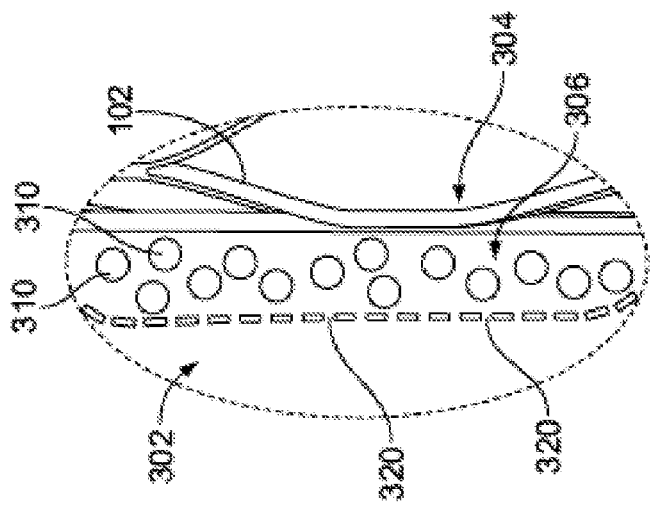
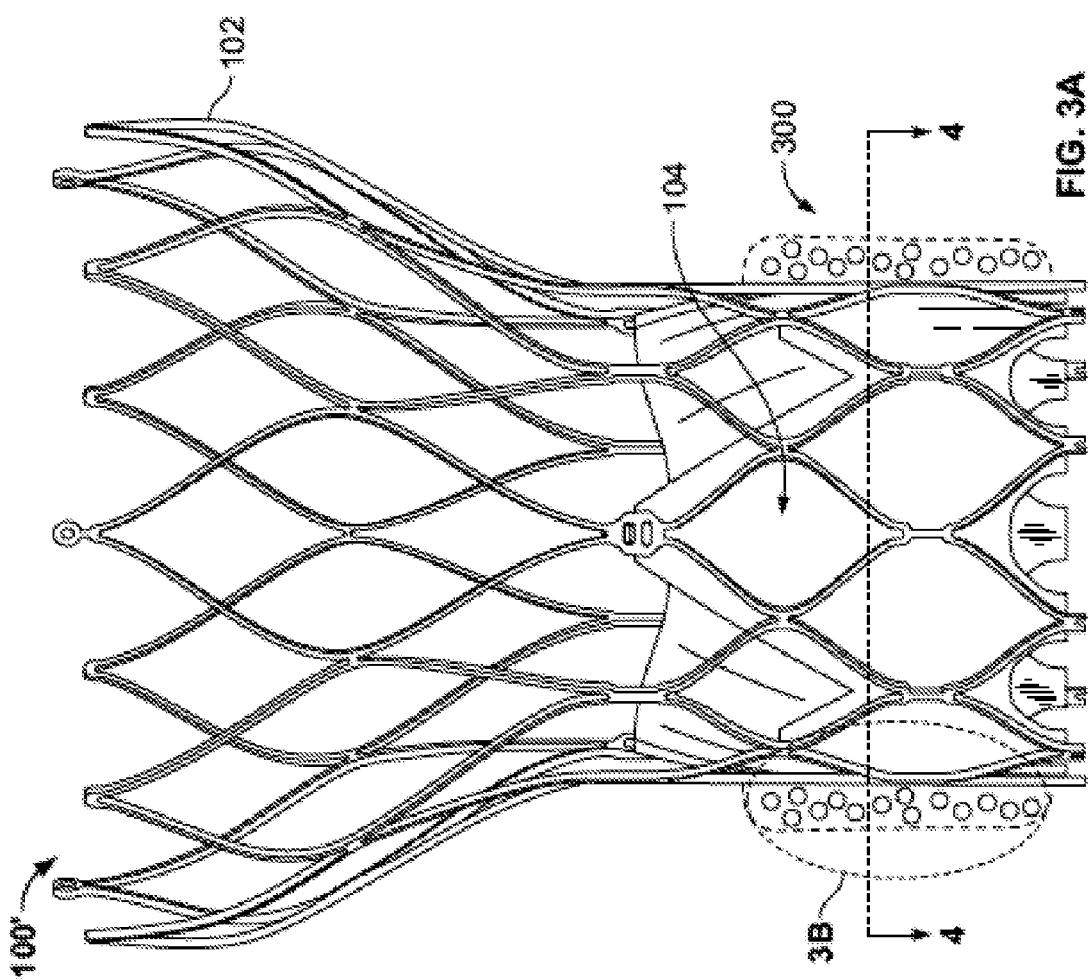

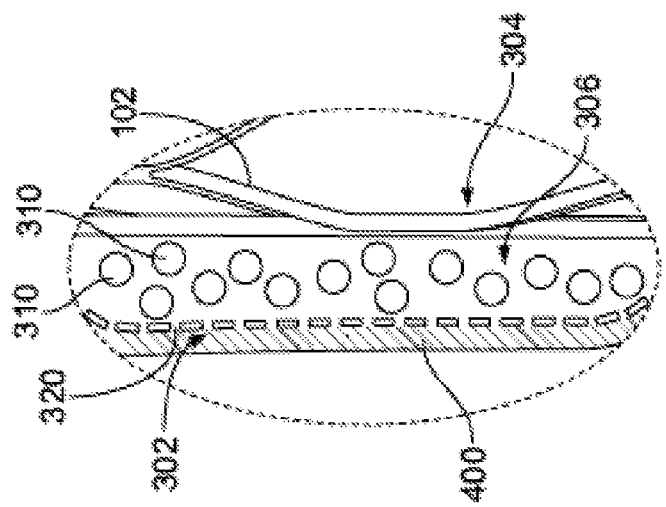
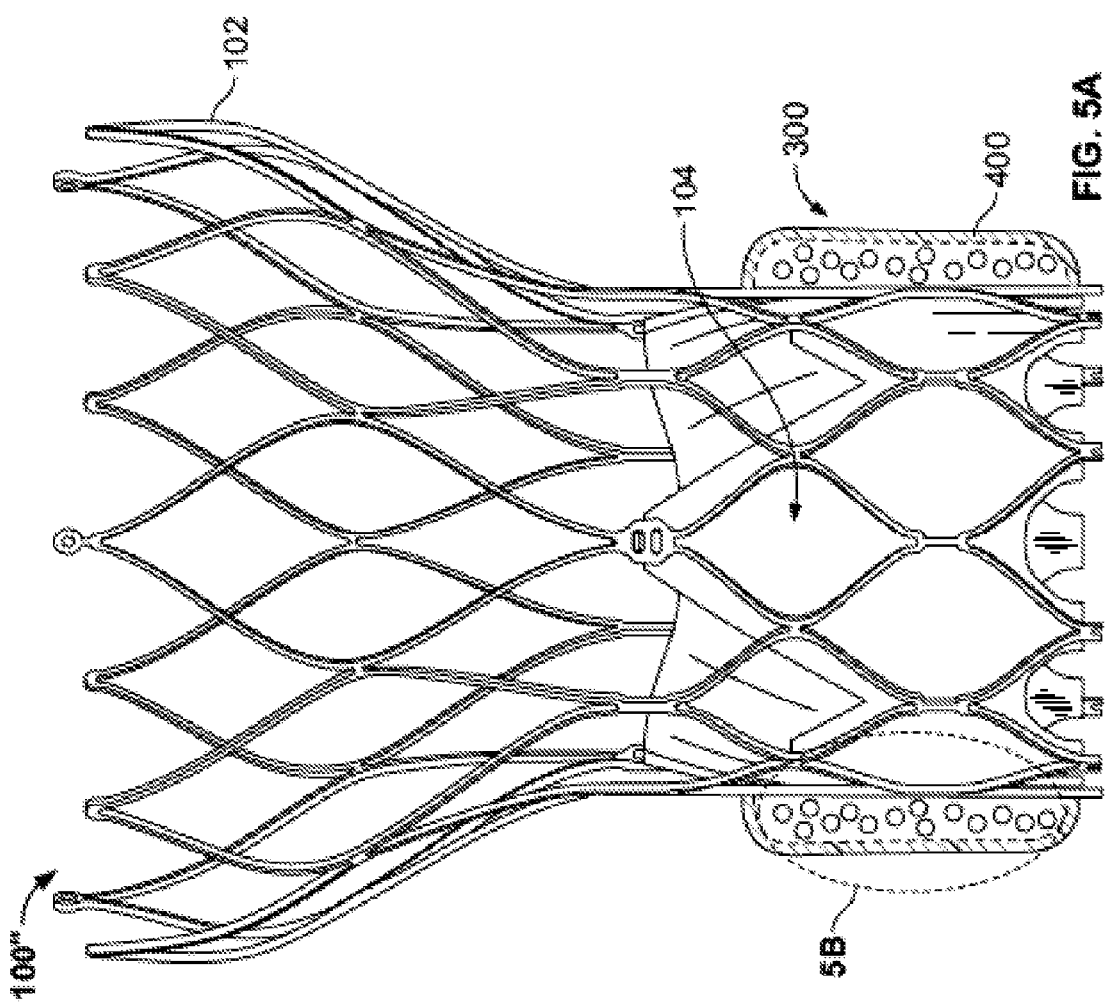
FIG. 5B
FIG. 5A

PROSTHETIC HEART VALVE WITH EXPANDABLE MICROSPHERES

CROSS-REFERENCE TO RELATED APPLICATIONS

The present application claims the benefit of the filing date of U.S. Provisional Patent Application No. 61/770,502 filed Feb. 28, 2013, the disclosure of which is hereby incorporated by reference herein.

BACKGROUND OF THE DISCLOSURE

The present disclosure relates to heart valve replacement and, in particular, to collapsible prosthetic heart valves. More particularly, the present disclosure relates to collapsible prosthetic transcatheter heart valves which minimize or reduce paravalvular leaks.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are ordinarily mounted: a self-expanding stent and a balloon-expandable stent. To place such valves into a delivery apparatus and ultimately into a patient, the valve is first collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the valve, assuring its proper location, and then expanding a balloon positioned within the valve stent. For self-expanding valves, on the other hand, the stent automatically expands as a sheath covering the valve is withdrawn.

Despite the various improvements that have been made to collapsible prosthetic heart valves, conventional devices suffer from shortcomings. For example, in some conventional prosthetic valves a cuff is attached to the stent. After implantation, gaps formed between the cuff and the site of implant may cause complications such as paravalvular leakage ("PV leak"), or blood flowing through a channel between the structure of the implanted valve and cardiac tissue as a result of a lack of appropriate sealing. This leakage can have adverse clinical outcomes. To reduce these adverse events, a valve should seal and adequately anchor within the annulus.

BRIEF SUMMARY OF THE DISCLOSURE

According to an embodiment of the disclosure, a prosthetic heart valve for replacement of a native valve includes a stent having an outer side and an inner side and a valve assembly mounted to the stent. A cuff is coupled to the stent and at least partially positioned on the outer side of the stent. The cuff forms at least one pocket. The prosthetic heart valve also includes a plurality of expandable microspheres confined within the at least one pocket.

According to another embodiment of the disclosure a prosthetic heart valve for replacement of a native valve includes a stent having an outer side and an inner side, and a valve assembly mounted to the stent. A cuff is coupled to the stent and at least partially positioned on the outer side of the stent. The cuff forms at least one pocket. The prosthetic heart valve also includes a biocompatible expandable material confined within the at least one pocket.

BRIEF DESCRIPTION OF THE DRAWINGS

Various embodiments of the presently disclosed prosthetic heart valve may be more fully understood with reference to the following detailed description when read with the accompanying drawings, in which:

FIG. 3A is a front view of a prosthetic heart valve according to an embodiment of the disclosure;

FIG. 3B is an enlarged partial view of the prosthetic heart valve of FIG. 3A;

FIG. 5A is a front view of a prosthetic heart valve according to an embodiment of the disclosure; and FIG. 5B is an enlarged partial view of the prosthetic heart valve of FIG. 5A.

DETAILED DESCRIPTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. Like numbers refer to similar or identical elements throughout.

Figure 1:
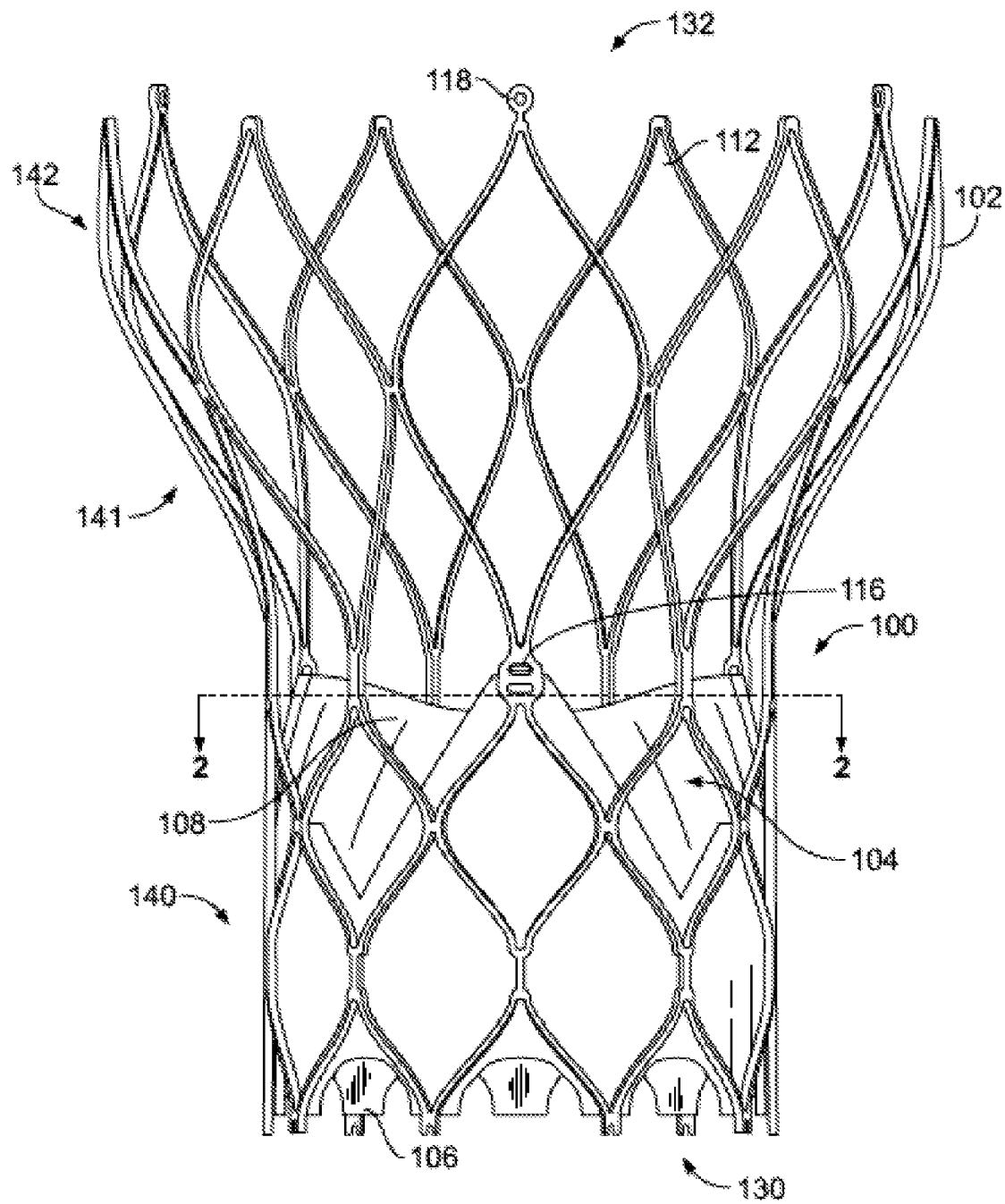
FIG. 1 is a front view of a collapsible prosthetic heart valve according to the prior art.

FIG. 1 shows a known collapsible stent-supported prosthetic heart valve 100. The prosthetic heart valve 100 is designed to replace the function of a native aortic valve of a patient. Examples of collapsible prosthetic heart valves are described in International Patent Application Publication No. WO/2009/042196; U.S. Pat. No. 7,018,406; and U.S. Pat. No. 7,329,278, the disclosures of all of which are hereby incorporated herein by reference.

The prosthetic heart valve will be discussed in more detail with reference to FIG. 1. It will also be noted that while the disclosure herein is predominately discussed in terms of a tricuspid valve and a stent having a shape as illustrated in FIG. 1, the valve could be a bicuspid valve, such as the mitral valve, and the stent could have different shapes, such as a flared or conical annulus section, a more or less bulbous aortic section, a differently shaped transition section between the aortic section and the annulus section, and may or may not be collapsible.

The prosthetic heart valve 100 includes a stent constructed as a frame 102, which may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyamides.

The stent 102 extends from a proximal or annulus end 130 to a distal or aortic end 132, and includes an annulus section 104 adjacent the proximal end 130 and an aortic section 142 adjacent the distal end 132. The annulus section 104 has a relatively small cross-section in the expanded condition, while the aortic section 142 has a relatively large cross-section in the expanded condition. The annulus section 104 may be in the form of a cylinder having a substantially constant diameter along its length. A transition section 141 may taper outwardly from the annulus section 104 to the aortic section 142. Each of the sections of the stent 102 includes a plurality of cells 112 connected to one another in one or more annular rows around the stent 102. For example, as shown in FIG. 1, the annulus section 104 may have two annular rows of complete cells 112 and the aortic section 142 and the transition section 141 may each have one or more annular rows of complete or partial cells 112. The cells 112 in the aortic section 142 may be larger than the cells 112 in the annulus section 104. The larger cells 112 in the aortic section 142 better enable the prosthetic valve 100 to be positioned without the stent structure 102 interfering with blood flow to the coronary arteries.

The stent 102 may include one or more retaining elements 118 at the distal end 132 thereof, the retaining elements 118 being sized and shaped to cooperate with retaining structures provided on a deployment device (not shown). The engagement of the retaining elements 118 with the retaining structures on the deployment device helps maintain the prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and during deployment. One such deployment device is shown in U.S. Patent Publication No. 2012/0078352, the entire contents of which are hereby incorporated by reference herein.

The stent 102 may also include a plurality of commissure points 116 for mounting the commissures (not identified), where two leaflets 108 come together, to the stent 102. As can be seen in FIG. 1, the commissure points 116 may lay at the intersection of four cells 112, two of the cells 112 being adjacent one another in the same annular row, and the other two cells 112 being in different annular rows and lying in end-to-end relationship. In one embodiment, the commissure points 116 are positioned entirely within the annulus section 104 or at the juncture of annulus section 104 and the transition section 141. The commissure points 116 may include one or more eyelets which facilitate the suturing of the leaflet commissure to the stent.

The prosthetic heart valve 100 includes a valve assembly 140 positioned in the annulus section 104. The valve assembly 140 may be mounted to the stent 102 by suturing the commissures of the leaflets 108 to the commissure points 116 and suturing other portions of the valve assembly 140 to the stent 102, or by other methods known in the art. The valve assembly 140 may include a cuff 106 and a plurality of leaflets 108 which collectively function as a one-way valve by coapting with one another. FIG. 1 illustrates a prosthetic heart valve for replacing a native tricuspid valve, such as the aortic valve. Accordingly, the prosthetic heart valve 100 is shown in FIG. 1 with three leaflets 108, as well as three commissure points 116. However, it will be appreciated that the prosthetic heart valves according to aspects of the disclosure may have a greater or lesser number of leaflets 108 and commissure points 116. The valve assembly 140 may be wholly or partly formed of any suitable biological material or polymer. Examples of biological materials suitable for the valve assembly 140 include, but are not limited to, porcine or bovine pericardial tissue. Examples of polymers suitable for the valve assembly 140 include, but are not limited to, polyurethane, silicone, PTFE and polyester. In at least some examples, portions of valve assembly 140, a cuff and the suture used may include an ultra high molecular weight polyethylene. An example of one such valve assembly 140 is disclosed in U.S. Patent Publication No. 2010/0185277, the entire contents of which are hereby incorporated by reference herein.

Although the cuff 106 is shown in FIG. 1 as being disposed on the lumenal or inner surface of the annulus section 104, it is contemplated that the cuff 106 may be disposed on the ablumenal or outer surface of annulus section 104, or may cover all or part of either or both of the lumenal and ablumenal surfaces of the annulus section 104. Both the cuff 106 and the leaflets 108 may be wholly or partly formed of any suitable biological material or polymer, including those, such as PTFE, described above in connection with the prosthetic heart valve 100. Additionally, the cuff 106 may be formed from polyurethane copolymers or include ultra high molecular weight polyethylene.

As is shown in FIG. 1, in one example the entirety of the valve assembly 140, including the leaflet commissures, is positioned in the annulus section 104 of the stent 102. When opened, the leaflets may extend further into the transition region 141 or may be designed such that they remain substantially completely within the annulus region 104. In this embodiment, substantially the entirety of the valve assembly 140 is positioned between the proximal end 130 of stent 102 and the commissure points 116, and none of the valve assembly is positioned between the commissure points 116 and the distal end 132 of the stent 102.

In operation, the embodiments of the prosthetic heart valve 100 described above may be used to replace a native heart valve, such as the aortic valve, a surgical heart valve or a heart valve that has undergone a surgical procedure. The prosthetic heart valve 100 may be delivered to the desired site (e.g., near a native aortic annulus) using any suitable delivery device. During delivery, the prosthetic heart valve 100 is disposed inside the delivery device in the collapsed condition. The delivery device may be introduced into a patient using any known procedures, such as a transfemoral, transapical or transseptal approach. Once the delivery device has reached the target site, the user may deploy the prosthetic heart valve 100. Upon deployment, the prosthetic heart valve 100 expands into secure engagement within the native aortic annulus. When the prosthetic heart valve 100 is properly positioned inside the heart, it works as a one-way valve, allowing blood to flow in one direction and preventing blood from flowing in the opposite direction.

Problems may be encountered when implanting the prosthetic heart valve 100. For example, in certain procedures, the prosthetic heart valve 100 may be implanted in a native valve annulus without first resecting the native valve leaflets. The prosthetic heart valve 100 may have critical clinical issues because of the nature of stenotic leaflets that are left in place. Additionally, patients with uneven calcification, bicuspid aortic valve disease, and/or valve insufficiency could not be treated well, if at all, with the current collapsible valve designs.

The reliance on unevenly calcified leaflets for proper valve placement and seating could lead to several problems, such as PV leak, which can have adverse clinical outcomes. To reduce these adverse events, the optimal valve would seal and anchor adequately without the need for excessive radial force that could harm nearby anatomy and physiology.

Figure 2:
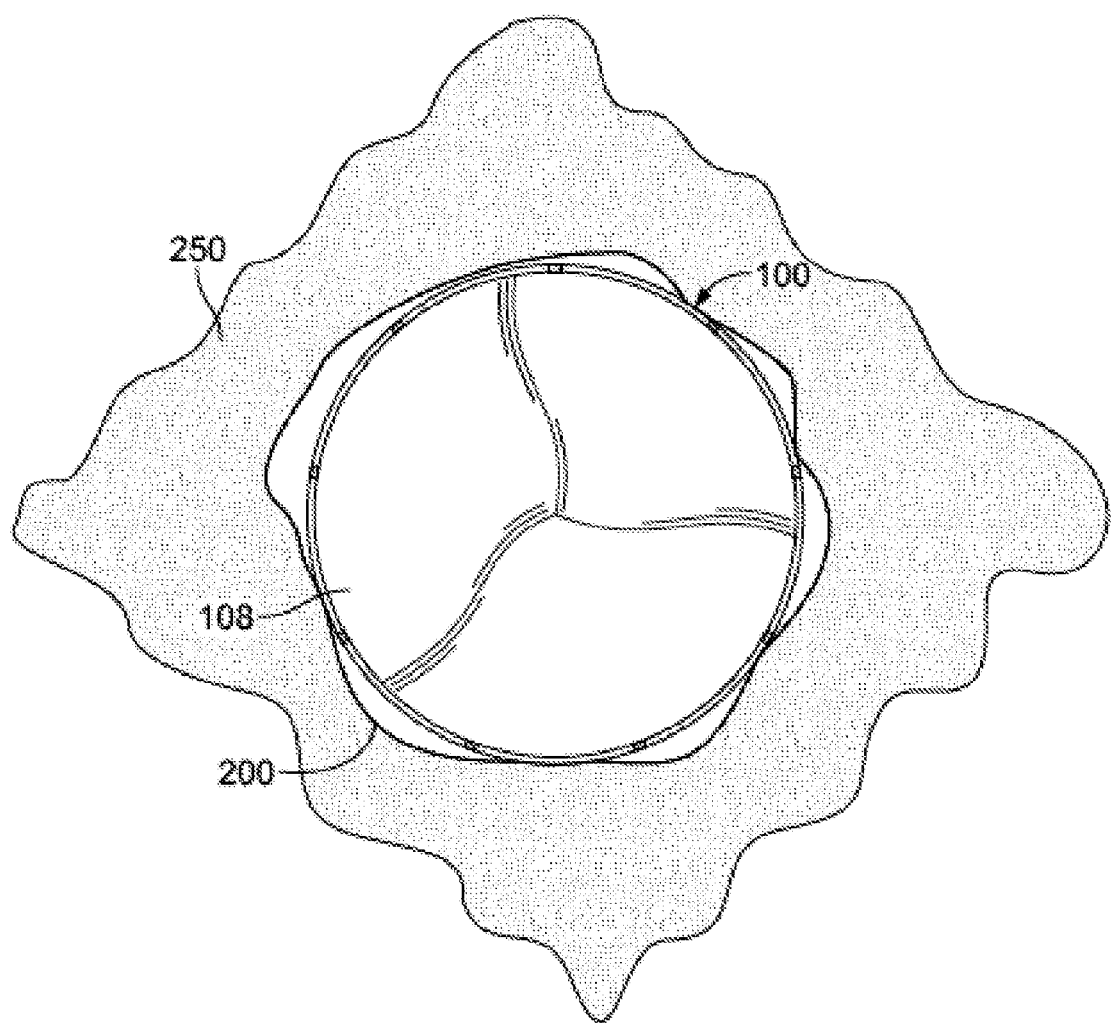
FIG. 2 is a top cross-sectional view of the prosthetic heart valve of FIG. 1 implanted in a patient taken along line 2-2.

FIG. 2 is a cross-sectional illustration of the prosthetic heart valve 100 having leaflets 108 disposed within the native valve annulus 250, taken along line A-A shown in FIG. 1. As seen in FIG. 2, the substantially circular annulus section 104 of the stent 102 is disposed within a non-circular native valve annulus 250. At certain locations around the perimeter of the prosthetic heart valve 100, gaps 200 form between the heart valve 100 and the native valve annulus 250. Blood flowing through these gaps and around the valve assembly 140 of the prosthetic heart valve 100 can result in PV leak or regurgitation and other inefficiencies which can reduce cardiac performance. Such improper fitment may be due to suboptimal native valve annulus geometry due, for example, to calcification of the native valve annulus 250 or due to unresected native leaflets.

FIG. 3A illustrates a prosthetic heart valve 100' according to an embodiment of the disclosure including an external cuff 300 with an expandable component in a dry, unexpanded state. As will be described below, the external cuff 300 with the expandable component allows for superior sealing between the perimeter of the prosthetic heart valve 100' and native valve annulus 250.

The stent 102 includes an external cuff 300 at least on the abluminal surface of the stent 102. In one embodiment, the external cuff 300 is a separate component from the cuff 106 of valve assembly 140 described above. In another embodiment, the external cuff 300 is a part of the cuff 106 of the valve assembly 140. In the latter embodiment, at least a portion of the combined external cuff 300 and cuff 106 is on the abluminal surface of the stent 102. As best illustrated in FIG. 3B, the external cuff 300 includes an outer portion 302 and an inner portion 304, each being external to the stent 102 and forming a pocket 306 enclosing an expandable component within the pocket. The pocket 306 may extend around the entire circumference of the stent 102, or around selected regions of the stent. The expandable component may be, for example, granules of different shapes and sizes. In the illustrated embodiment, the expandable component comprises a plurality of microspheres 310 within the pocket 306. In other embodiments, the expandable component may comprise other shapes, such as cylinders, cubes, or sheets. The outer portion 302 of the external cuff 300, facing away from the stent 102, is porous. The pores 320 may be constant or variable in size, but most or all of the pores 320 are smaller than the diameter of the smallest microsphere 310 such that no microsphere 310 can migrate out of the external cuff 300 and freely enter the circulation once the prosthetic heart valve 100' is implanted in a patient. However, the pores 320 are large enough to allow for fluids, such as blood, to enter and exit the pocket 306 of the external cuff 300. In one embodiment, the pocket 306 of the external cuff 300 containing the microspheres 310 is generally confined to the annulus section 104 of the stent 102.

Additionally, although the external cuff 300 shown in FIGS. 3A-B is entirely on the abluminal surface of the stent 102, the inner portion of the external cuff 300 may reside on the lumenal surface of the stent 102 such that the microspheres 310 can migrate within the pocket of the external cuff 300 and through an open cell 112 of the stent 102. As described above, the external cuff 300 may be an entirely separate structure from the cuff 106 described in relation of the valve assembly 140, or may be part of the cuff 106. Similarly, although only the outer surface 302 of the external cuff 300 is shown as being porous, the entire external cuff 300 may be porous. As shown in FIGS. 3A-B, the external cuff 300 may form one pocket 306 through which all microspheres 310 may migrate. Alternatively, more than one pocket 306 may be formed in the external cuff 300, for example by sewing the external cuff 300 along the cells 112 of the stent 102. In this embodiment, the microspheres 310 within a first pocket are able to move within the first pocket, but are generally unable to migrate into a second pocket of the cuff 300 that is sealed, for example by a suture, from the first pocket.

Figure 4:
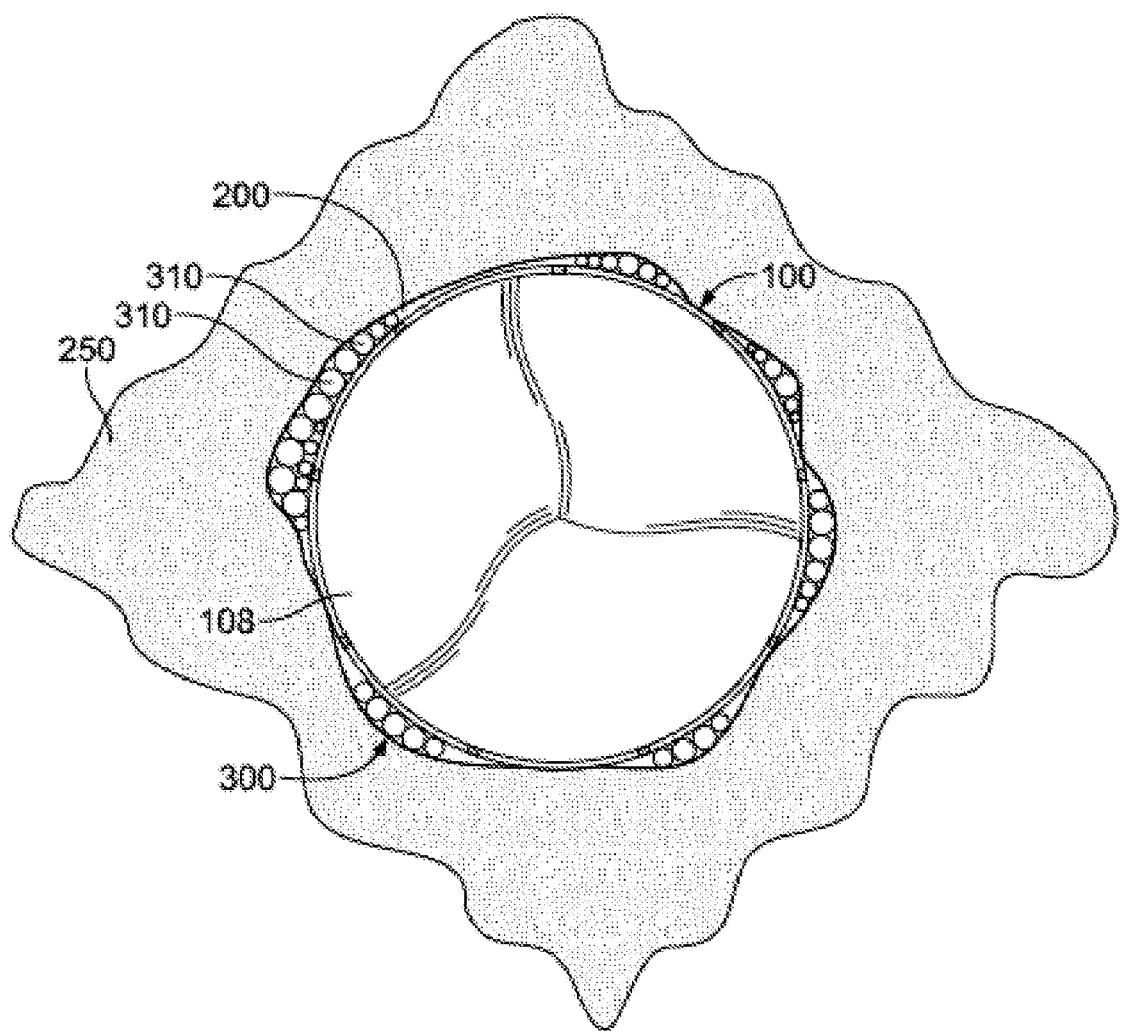
FIG. 4 is a top cross-sectional view of the prosthetic heart valve of FIG. 3A implanted in a patient taken along line 4-4.

FIG. 4 is a cross-sectional illustration of the prosthetic heart valve 100' disposed within the native valve annulus 250. As seen in FIG. 4, the annulus section 104 of the stent 102 is substantially circular and disposed within a non-circular native valve annulus 250. In this illustration, the prosthetic heart valve 100' has been implanted and the microspheres 310 near the gaps 200 have expanded and conformed to fill the gaps 200 that were previously disposed between the outer surface of heart valve 100' and the native valve annulus 250. This expansion is the result of the interaction between blood and/or other bodily fluids flowing through the pores 320 and into the pocket 306 of the external cuff 300 and interacting with the microspheres 310 to cause expansion of the microspheres, explained in greater detail below. Notably, the microspheres 310 that are not located within a gap 200 are exposed to little or no blood, since a tight seal exists between the prosthetic heart valve 100' and the native valve annulus 250 where there are no gaps 200. Because these microspheres 310 are exposed to little or no blood, they do not expand, or expand only minimally, and do not put excessive radial forces on the native valve annulus 250.

The microspheres 310 may be biocompatible, hydrophilic, conformable, non-resorbable and expandable up to about 60 times of their dry state volume. The microspheres 310 may take the form of biocompatible spherical particles made of materials such as polyvinyl alcohol (PVA) and gelatin with chemically cross-linkable functionality (e.g., acryloyl and acrylamido groups). Upon coming into contact with an ionic solution, such as blood, the microspheres 310 expand irreversibly.

The following materials may be used in forming the expandable components, such as microspheres 310, suitable for use with the present disclosure, and are not to be considered limiting but rather illustrative: tris-acryl cross-linked with gelatin, commercially available from Merit Medical Systems, Inc. (South Jordan, Utah) under the name Embosphere®; PVA polymers, commercially available from Boston Scientific (Natick, Mass.) under the name Contour SE®; acrylamido PVA polymers, commercially available from Biocompatibles International (Oxford, Conn.) under the name Bead Block™; PVA-sodium acrylate copolymers, commercially available from Merit Medical Systems, Inc. (South Jordan, Utah) under the name QuadraSphere®; hydrogel core coated with Polyzene®-F or poly[bis(trifluroethoxy) phosphazene], commercially available from CeloNova BioSciences (San Antonio, Tex.) under the name Embozene®; and PVA hydrogels, commercially available from Angiodynamics (Latham, N.Y.) under the name LC Bead™.

More generally speaking, expandable components, such as microspheres 310, suitable for use with the current disclosure may be formed of biocompatible and irreversibly expandable materials, such as PVA materials, for example non-chemically cross-linked hydrogel comprised of PVA-sodium acrylate copolymers. PVA-sodium acrylate copolymers can be synthesized by free-radical copolymerization procedures. Functional vinyl monomers such as methyl acrylate, 1,2-dicarboxylic acid such as dimethyl fumarate, and 1,1-dicarboxylic acid such as diethyl methylenemalonate can be copolymerized with vinyl acetate by using a free-radical initiator such as 2,2'-azobisobutyronitrile (AIBN) catalyzed by strong base such as sodium hydroxide (NaOH).

The microspheres 310 may be formed of a material that has a relatively slow expansion rate compared to the time required for the delivery and implantation procedures. As the prosthetic heart valve 100' is implanted, it may be exposed to fluid. For example, during delivery of the prosthetic heart valve 100' to the native valve annulus 250, blood or other fluid may pass through the pores 320 of the external cuff 300 and contact the microspheres 310 prior to the prosthetic heart valve 100' being finally positioned. The microspheres 310 may expand slowly such that contact of blood or other fluid with the microspheres 310 during the delivery process causes only minimal or negligible expansion of the microspheres 310. To further this goal, the external cuff 300 may be coated in a salt solution such that salt crystals are located within or near the pores 320 of the external cuff 300. Fluid passing through the pores 320 during delivery of the prosthetic heart valve 100' first interacts with the salt crystals prior to entering the pocket 306 of the external cuff 300 through the pores 320. Such a coating of salt solution may delay the interaction of blood or other fluid with the microspheres 310 during the delivery process, helping to minimize the opportunity for the microspheres 310 to expand before the prosthetic valve 100' is in its final position within the native valve annulus 250. This salt solution may be particularly effective when the valve is stored in dry conditions prior to implantation. Any water soluble salts, such as sodium chloride or potassium chloride, may be suitable.

Although the disclosure uses the term "microspheres," one skilled in the art would recognize that expandable PVA (or other expandable biocompatible material) does not necessarily need to be multiple spherical elements. For example, an expandable or swellable sheet-like or cylindrical gel could be used in place of multiple discrete microspheres 310 to achieve substantially the same result. Similarly, the expandable PVA may comprise granules of different shapes and sizes.

In another embodiment of the disclosure, a prosthetic heart valve 100" includes an external cuff 300 with expandable microspheres 310 in a dry, unexpanded state, the external cuff 300 having a protective layer 400, illustrated in FIG. 5A. The protective layer 400 covers the external cuff 300, as best seen in FIG. 5B, and more specifically covers the pores 320 in the external cuff 300 such that fluid cannot enter the pocket 306 of the external cuff 300 and interact with the microspheres 310 while the protective layer 400 is affixed to the external cuff 300. The protective layer 400 may be formed of any material that will prevent water or other fluids, such as formaldehyde or glutaraldehyde storage solutions, from crossing the barrier of the protective layer 400. Suitable materials for such a protective layer 400 may include, without limitation, polyethylene, polylactic acid, polypropylene, etc. The protective layer 400 may also include hydrophobic material to increase the effectiveness of the protection against fluid migrating through the protective layer 400 and into the microspheres 310. The protective layer 400 may also include an adhesive on the surface facing the external cuff 300, such that the protective layer 400 may be applied to the external cuff 300 prior to storage in solution, and peeled off prior to implantation into a patient.

The protective layer 400 may be especially useful for cases in which hydrated tissue valves are used for the prosthetic heart valve 100" as opposed to dry valves. When hydrated tissue valves are used, it may be useful to store the prosthetic heart valve 100" in a solution such as formaldehyde, for example during shipping or prior to implantation. Without the protective layer 400, solution could flow through the pores 320 of external cuff 300 and cause premature and irreversible expansion of the microspheres 310, reducing the ability of the microspheres 310 to expand after implantation and thus reducing the ability for enhanced sealing. This premature expansion could also result in other problems, such as difficulty in loading the prosthetic heart valve 100" into a delivery device in a collapsed state. In this embodiment, the protective layer 400 could be removed from the external cuff 300 at a point just prior to implanting the prosthetic heart valve 100" into the patient. The microspheres 310 would thus still be in a dry state prior to implantation.

Paragraph A: A prosthetic heart valve for replacement of a native valve comprises: a stent having an outer side and an inner side; a valve assembly mounted to the stent; a cuff coupled to the stent and at least partially positioned on the outer side of the stent, the cuff forming at least one pocket; and a plurality of expandable microspheres confined within the at least one pocket.

Paragraph B: The prosthetic heart valve of Paragraph A, wherein the at least one pocket is formed between an inner side of the cuff and an outer side of the cuff.

Paragraph C: The prosthetic heart valve of Paragraph B, wherein the outer side of the cuff is positioned external to the outer side of the stent and the inner side of the cuff is positioned external to the outer side of the stent.

Paragraph D: The prosthetic heart valve of Paragraph B, wherein the outer side of the cuff is positioned external to the outer side of the stent and the inner side of the cuff is positioned internal to the inner side of the stent.

Paragraph E: The prosthetic heart valve of Paragraph B, wherein the outer side of the cuff defines a plurality of pores.

Paragraph F: The prosthetic heart valve of Paragraph E, wherein each microsphere has a diameter and each pore has a maximum width, the maximum width of each pore being less than the diameter of each microsphere.

Paragraph G: The prosthetic heart valve of Paragraph E, wherein the outer side of the cuff includes salt crystals.

Paragraph H: The prosthetic heart valve of Paragraph B, further comprising a protective layer coupled to the outer side of the cuff configured to prevent fluid crossing from the outer side of the cuff into the at least one pocket.

Paragraph I: The prosthetic heart valve of Paragraph H, wherein the protective layer is formed from a hydrophobic material.

Paragraph J: The prosthetic heart valve of Paragraph H, wherein the protective layer includes an adhesive on an inner side thereof configured to adhere to the outer side of the cuff.

Paragraph K: The prosthetic heart valve of Paragraph A, further comprising at least one suture coupling the cuff to the stent, the at least one suture forming a plurality of pockets.

Paragraph L: The prosthetic heart valve of Paragraph K, further comprising: a first group of microspheres within one of the plurality of pockets; and a second group of microspheres within a second of the plurality of pockets; wherein the at least one suture separates the first group of microspheres from the second group of microspheres.

Paragraph M: The prosthetic heart valve of Paragraph A, wherein the plurality of expandable microspheres are at least partially formed of polyvinyl alcohol.

Paragraph N: A prosthetic heart valve for replacement of a native valve comprising: a stent having an outer side and an inner side; a valve assembly mounted to the stent; a cuff coupled to the stent and at least partially positioned on the outer side of the stent, the cuff forming at least one pocket; and a biocompatible expandable material confined within the at least one pocket.

Paragraph O: The prosthetic heart valve of Paragraph N, wherein the biocompatible expandable material is formed as a sheet.

Paragraph P: The prosthetic heart valve of Paragraph O, wherein the sheet of biocompatible expandable material is cylindrical.

Paragraph Q: The prosthetic heart valve of Paragraph O, further comprising at least one suture coupling the cuff to the stent, the at least one suture forming a plurality of pockets.

Paragraph R: The prosthetic heart valve of Paragraph Q, wherein at least one of the plurality of pockets contains a portion of the sheet of biocompatible expandable material.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure.

The invention claimed is:

1. A prosthetic heart valve for replacement of a native valve comprising:
    a stent having an outer side and an inner side;
    a valve assembly mounted to the stent;
    a cuff coupled to the stent and at least partially positioned on the outer side of the stent, the cuff including a plurality of pockets sealed from one another; and
    a plurality of expandable microspheres confined within the plurality of pockets.

2. The prosthetic heart valve of claim 1, wherein the plurality of pockets are formed between an inner side of the cuff and an outer side of the cuff.

3. The prosthetic heart valve of claim 2, wherein the outer side of the cuff is positioned external to the outer side of the stent and the inner side of the cuff is positioned external to the outer side of the stent.

4. The prosthetic heart valve of claim 2, wherein the outer side of the cuff is positioned external to the outer side of the stent and the inner side of the cuff is positioned internal to the inner side of the stent.

5. The prosthetic heart valve of claim 2, wherein the outer side of the cuff defines a plurality of pores.

6. The prosthetic heart valve of claim 5, wherein each microsphere has a diameter and each pore has a maximum width, the maximum width of each pore being less than the diameter of each microsphere.

7. The prosthetic heart valve of claim 5, wherein the outer side of the cuff includes salt crystals.

8. The prosthetic heart valve of claim 2, further comprising a protective layer coupled to the outer side of the cuff configured to prevent fluid crossing from the outer side of the cuff into the plurality of pockets.

9. The prosthetic heart valve of claim 8, wherein the protective layer is formed from a hydrophobic material.

10. The prosthetic heart valve of claim 8, wherein the protective layer includes an adhesive on an inner side thereof configured to adhere to the outer side of the cuff.

11. The prosthetic heart valve of claim 1, further comprising at least one suture coupling the cuff to the stent, the at least one suture forming the plurality of pockets.

12. The prosthetic heart valve of claim 11, further comprising:
    a first group of microspheres within one of the plurality of pockets; and
    a second group of microspheres within a second of the plurality of pockets, wherein the at least one suture separates the first group of microspheres from the second group of microspheres.

13. The prosthetic heart valve of claim 1, wherein the plurality of expandable microspheres are at least partially formed of polyvinyl alcohol.

14. A prosthetic heart valve for replacement of a native valve comprising:
    a stent having an outer side and an inner side;
    a valve assembly mounted to the stent;
    a cuff coupled to the stent and at least partially positioned on the outer side of the stent, the cuff being coupled to the stent by at least one suture, the at least one suture forming a plurality of pockets sealed from one another; and
    a biocompatible expandable material confined within at least one of the plurality of pockets.

15. The prosthetic heart valve of claim 14, wherein the biocompatible expandable material is formed as a sheet.

16. The prosthetic heart valve of claim 15, wherein the sheet of biocompatible expandable material is cylindrical.

17. The prosthetic heart valve of claim 15, wherein at least one of the plurality of pockets contains a portion of the sheet of biocompatible expandable material.

\* \* \* \* \*